United States Patent [19]

Farge et al.

[11] 4,108,999
[45] Aug. 22, 1978

[54] THIAZOLO[3,4-b]ISOQUINOLINE DERIVATIVES, PHARMACEUTICAL COMPOSITIONS CONTAINING THEM AND PHARMACEUTICAL METHODS USING THEM

[75] Inventors: Daniel Farge, Sylvestres Thiais; Alain Jossin, Saint Cloud; Gérard Ponsinet, Sucy-en-Brie; Daniel Reisdorf, Republique-Thiais, all of France

[73] Assignee: Rhone-Poulenc Industries, Paris, France

[21] Appl. No.: 770,757

[22] Filed: Feb. 22, 1977

[51] Int. Cl.$^2$ .................. C07D 513/14; A61K 31/47
[52] U.S. Cl. ......................... 424/258; 260/288 CF; 260/283 S; 260/283 CN; 260/289 C; 260/289 D; 260/287 D; 260/286 R; 260/283 R; 260/294.8 R
[58] Field of Search ............... 424/258; 260/288 CF, 260/283 S

[56] References Cited
U.S. PATENT DOCUMENTS 3,455,933   7/1969   Georgiadis et al. ................ 260/289
3,979,397   9/1976   Harsanyi et al. .............. 260/288 CF

FOREIGN PATENT DOCUMENTS 844,927   2/1977   Belgium.

Primary Examiner—Donald G. Daus
Assistant Examiner—Diana G. Rivers
Attorney, Agent, or Firm—Stevens, Davis, Miller & Mosher

[57] ABSTRACT

Thiazolo[3,4-b]isoquinoline derivatives of the formula:

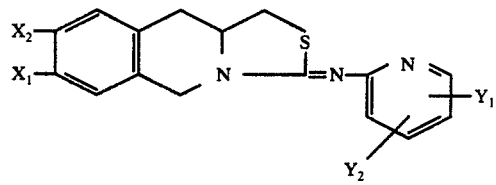

wherein $X_1$ represents hydrogen, halogen, methoxy or cyano, $X_2$ represents hydrogen, halogen or methoxy, or $X_1$ and $X_2$ together represent methylenedioxy, and $Y_1$ and $Y_2$ each represent hydrogen, halogen, alkyl of 1 through 4 carbon atoms, alkoxy of 1 through 4 carbon atoms, alkylthio of 1 through 4 carbon atoms, hydroxy, amino or diacetylamino, are new compounds useful as anti-ulcer agents.

9 Claims, No Drawings

THIAZOLO[3,4-b]ISOQUINOLINE DERIVATIVES, PHARMACEUTICAL COMPOSITIONS CONTAINING THEM AND PHARMACEUTICAL METHODS USING THEM

This invention relates to new therapeutically useful thiazolo[3,4-b]isoquinoline derivatives, to processes for their preparation and to pharmaceutical compositions containing them.

The new thiazolo[3,4-b]isoquinoline derivatives of the present invention are those of the general formula:

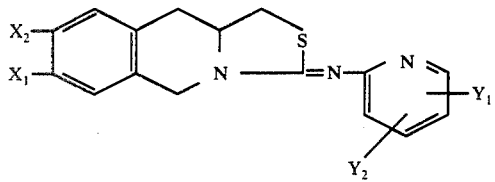

wherein $X_1$ represents a hydrogen or halogen atom or a methoxy or cyano radical, $X_2$ represents a hydrogen or halogen atom or a methoxy radical, or $X_1$ and $X_2$ together represent a methylenedioxy radical, and $Y_1$ and $Y_2$ are the same or different and each represents a hydrogen or halogen atom, an alkyl radical containing 1 to 4 carbon atoms, an alkoxy radical containing 1 to 4 carbon atoms, an alkylthio radical containing 1 to 4 carbon atoms, or a hydroxy, amino or diacetylamino radical, and acid addition salts thereof.

The compounds of general formula I can exist in (R)- and (S)-forms and the invention includes both such forms and mixtures thereof.

According to a feature of the present invention, the thiazolo[3,4-b]isoquinoline derivatives of general formula I wherein $X_1$ represents a hydrogen atom or a methoxy radical, $X_2$ represents a hydrogen or halogen atom or a methoxy radical, or $X_1$ and $X_2$ together represent a methylenedioxy radical, and $Y_1$ and $Y_2$ are the same or different and each represents a hydrogen or halogen atom or an alkyl radical containing 1 to 4 carbon atoms, an alkoxy radical containing 1 to 4 carbon atoms, an alkylthio radical containing 1 to 4 carbon atoms or a hydroxy radical, are prepared by the process which comprises the cyclisation of a 1,2,3,4-tetrahydroisoquinoline derivative of the general formula:

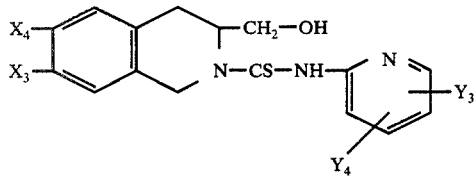

wherein $X_3$ represents a hydrogen atom or a methoxy radical, $X_4$ represents a hydrogen or halogen atom or a methoxy radical, or $X_3$ and $X_4$ together represent a methylenedioxy radical, and $Y_3$ and $Y_4$ are the same or different and each represents a hydrogen or halogen atom, an alkyl radical containing 1 to 4 carbon atoms, an alkoxy radical containing 1 to 4 carbon atoms, an alkylthio radical containing 1 to 4 carbon atoms or the hydroxy radical.

The reaction is generally carried out by heating the compound of general formula II in an acid medium. It is particularly advantageous to carry out the reaction at a temperature between 65° and 100° C in an aqueous inorganic acid, for example in hydrochloric acid.

The 1,2,3,4-tetrahydroisoquinoline derivative of general formula II can be obtained by reacting an isothiocyanate of the general formula:

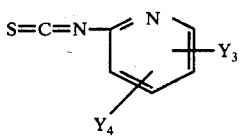

(wherein $Y_3$ and $Y_4$ are as hereinbefore defined) with a 3-hydroxymethyl-1,2,3,4-tetrahydroisoquinoline derivative of the general formula:

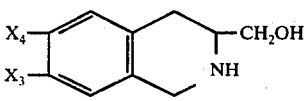

wherein $X_3$ and $X_4$ are as hereinbefore defined. The reaction is generally carried out in an organic solvent such as an alcohol, for example ethanol, at a temperature between 20° and 70° C.

The isothiocyanate of general formula III wherein $Y_3$ and $Y_4$ represent hydrogen atoms can be prepared in accordance with the method described by A. Fairfull and D. Peak, J. Chem. Soc., 798 (1955).

The isothiocyanates of general formula III wherein at least one of the symbols $Y_3$ and $Y_4$ is other than a hydrogen atom can be obtained in accordance with methods described in the specification of British Pat. No. 1,444,558 and U.S. Pat. No. 3,900,480.

The 3-hydroxymethyl-1,2,3,4-tetrahydroisoquinoline derivatives of general formula IV can be obtained by reduction of a 1,2,3,4-tetrahydroisoquinoline derivative of the general formula:

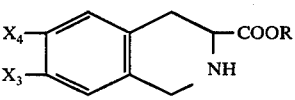

(wherein R represents a hydrogen atom or an alkyl radical containing from 1 to 4 carbon atoms, and $X_3$ and $X_4$ are as hereinbefore defined) or an acid addition salt thereof.

When R in general formula V represents a hydrogen atom, the reduction is preferably carried out using lithium aluminium hydride in tetrahydrofuran at a temperature between 20° and 70° C.

When R in general formula V represents an alkyl radical containing 1 to 4 carbon atoms, the reduction is preferably carried out by means of an alkali metal borohydride, such as sodium borohydride, in an organic solvent or in an aqueous-organic medium, such as a mixture of ethanol and water, and at a temperature between 10° and the reflux temperature of the reaction mixture.

The 1,2,3,4-tetrahydroisoquinoline derivatives of general formula V wherein R represents an alkyl radical containing 1 to 4 carbon atoms can be obtained by esterification of a 1,2,3,4-tetrahydroisoquinoline derivative of general formula V wherein R represents a hydrogen atom, by known methods for the conversion of an acid into an ester without affecting the rest of the molecule.

By the term "known methods" as used in this specification and accompanying claims is meant methods heretofore used or described in the chemical literature.

The 1,2,3,4-tetrahydroisoquinoline derivatives of general formula V wherein R represents a hydrogen atom and $X_3$ and $X_4$ are as hereinbefore defined can be prepared from a phenylalanine derivative of the general formula:

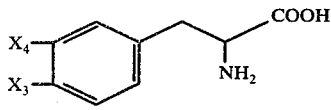

VI (wherein $X_3$ and $X_4$ are as hereinbefore defined) by application of the method described by A. Pictet and Th. Spengler, Chem. Ber., 44, 2030 (1911).

When the L-form of a phenylalanine derivative of general formula VI is used, the product of general formula I obtained via the compound of general formula V is in the (S)-form. When a phenylalanine derivative of general formula VI in the D-form is used, the product of general formula I is obtained in the (R)-form. When a mixture of the D- and L-forms of the phenylalanine derivative of general formula VI is used, the product of general formula I is obtained in the (R,S)-form.

According to a further feature of the invention, the thiazolo[3,4-b]isoquinoline derivatives of general formula I, wherein $X_1$ and $X_2$ are as hereinbefore defined and the symbols $Y_1$ and $Y_2$ each represent a hydrogen or halogen atom, an alkyl radical containing 1 to 4 carbon atoms, an alkoxy radical containing 1 to 4 carbon atoms, or a hydroxy or amino radical, are prepared by the process which comprises reacting an aminopyridine of the general formula:

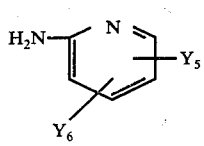

VII (wherein $Y_5$ and $Y_6$ are the same or different and each represents a hydrogen or halogen atom, an alkyl radical containing 1 to 4 carbon atoms, an alkoxy radical containing 1 to 4 carbon atoms, or a hydroxy or amino radical) with a salt of the general formula:

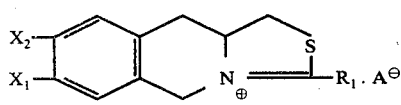

VIII (wherein $X_1$ and $X_2$ are as hereinbefore defined, $R_1$ represents a chlorine atom, an alkylthio radical containing 1 to 4 carbon atoms (preferably methylthio) or a benzylthio radical, and $A^{\ominus}$ represents an anion, such as a chloride, iodide, sulphate, tetrafluoroborate or fluorosulphonate ion. When $R_1$ represents a chlorine atom, $A^{\ominus}$ represents a chloride ion. When $R_1$ represents an alkylthio or benzylthio radical $A^{\ominus}$ represents an anion such as an iodide, sulphate, tetrafluoroborate or fluorosulphonate ion.

When $R_1$ represents a chlorine atom and $A^{\ominus}$ represents a chloride ion, the reaction is preferably carried out in an organic solvent, such as acetonitrile, in the presence of an alkaline condensation agent, such as triethylamine, at a temperature of about 20° C.

When $R_1$ represents an alkylthio or benzylthio radical and $A^{\ominus}$ represents an iodide, sulphate, tetrafluoroborate or fluorosulphonate ion, the reaction is preferably carried out in a basic organic solvent, such as pyridine, at a temperature of about 20° C.

The salt of general formula VIII wherein $R_1$ represents a chlorine atom and $A^{\ominus}$ represents a chloride ion can be obtained by the reaction of a chlorinating agent, such as phosgene, phosphorus pentachloride, thionyl chloride or oxalyl chloride, on a thiazolo[3,4-b]isoquinoline-3-thione derivative of the general formula:

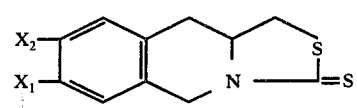

IX wherein $X_1$ and $X_2$ are as hereinbefore defined. The reaction is generally carried out in an organic solvent or a mixture of organic solvents, such as a mixture of toluene and tetrahydrofuran, at a temperature between 0° and 70° C.

The salts of the general formula VIII wherein $R_1$ represents an alkylthio or benzylthio radical and $A^{\ominus}$ represents an iodide, sulphate, tetrafluoroborate or fluorosulphonate anion can be obtained by the reaction of a reactive ester of the general formula:

X (wherein $R_2$ represents an alkyl radical containing 1 to 4 carbon atoms or a benzyl radical, and $A_1$ represents the residue of a reactive ester such as an iodine atom or an alkoxysulphonyloxy radical), or of triethyloxonium tetrafluoroborate or methyl fluorosulphonate, with a compound of general formula IX. The reaction is generally effected, optionally in the presence of an organic solvent such as methylene chloride, at a temperature of about 20° C.

The thiazolo[3,4-b]isoquinoline-3-thione derivatives of general formula IX wherein $X_1$ and $X_2$ are as hereinbefore defined (with the exception of those compounds wherein $X_1$ represents a cyano radical) can be obtained by the reaction of carbon disulphide, in a basic medium, with a 1,2,3,4-tetrahydroisoquinoline derivative of the general formula:

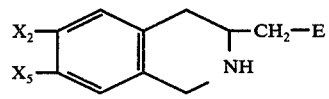

XI wherein $X_5$ represents a hydrogen or halogen atom or a methoxy radical, or $X_2$ and $X_5$ together represent a methylenedioxy radical, and E represents a halogen, e.g. bromine or chlorine, atom or a hydroxysulphonyloxy radical. The reaction is generally carried out in the presence of sodium or potassium hydroxide at a temperature of about 20° C.

The compounds of general formula XI can be obtained by the action of an inorganic acid on a 3-hydroxymethylisoquinoline derivative of general formula IV wherein $X_4$ is as hereinbefore defined and $X_3$ represents a hydrogen or halogen atom or a methoxy radical, or X₃ and X₄ together represent a methylenedioxy radical.

Compounds of general formula XI wherein E represents a hydroxysulphonyloxy radical are generally prepared by treatment of a said compound of general formula IV with sulphuric acid in an aqueous medium at a temperature of about 100° C, or in an organic solvent (such as dimethylformamide) in the presence of dicyclohexylcarbodiimide at a temperature of about 20° C.

Compounds of general formula XI wherein E represents a bromine atom are generally prepared by treatment of a said compound of general formula IV with concentrated aqueous hydrobromic acid (at least 40% and preferably 48% w/w) at the reflux temperature of the reaction mixture, and isolating the product of general formula XI as its hydrobromide.

Compounds of general formula XI wherein E represents a chlorine atom are generally prepared by treatment of a said compound of general formula IV with thionyl chloride in an organic solvent, such as chloroform, saturated with hydrogen chloride gas, and at the reflux temperature of the reaction mixture, and isolating the product of general formula XI as its hydrochloride.

The compounds of general formula IX wherein $X_1$ represents a cyano radical and $X_2$ is as hereinbefore defined can be obtained from a compound of the general formula:

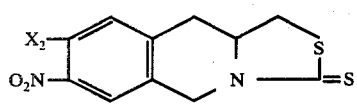

XII (wherein $X_2$ is as hereinbefore defined) by known methods for the conversion of a nitro radical to a cyano radical via the corresponding amine intermediate.

Compounds of general formula XII wherein $X_2$ is as hereinbefore defined can be obtained from a compound of general formula IX, wherein $X_1$ represents a hydrogen atom, by nitration. The nitration is generally carried out with a mixture of nitric and sulphuric acid at a temperature of about −20° C, or with nitronium fluoroborate in acetonitrile at a temperature of about 20° C, or with sodium nitrate in trifluoroacetic acid at a temperature of about 20° C, followed if desired by separation of the isomers obtained.

The compounds of general formula VII wherein $Y_5$ and $Y_6$ are as hereinbefore defined can be obtained in accordance with methods described in Heterocyclic compounds, Pyridine and derivatives, 14 Suppl. Part 3 (1974).

According to another feature of the invention, the thiazolo[3,4-b]isoquinoline derivatives of general formula I wherein $X_1$ represents a hydrogen or halogen atom or a cyano radical and $X_2$ represents a hydrogen or halogen atom, one only of the symbols $X_1$ and $X_2$ representing a hydrogen atom, and the symbols $Y_1$ and $Y_2$ each represent a hydrogen or halogen atom or an alkyl, alkoxy, alkylthio or hydroxy radical, are prepared by the process which comprises treating a compound of the general formula:

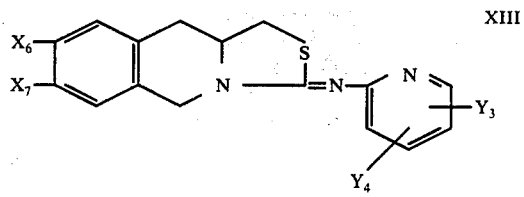

XIII (wherein $Y_3$ and $Y_4$ are as hereinbefore defined, one of the symbols $X_6$ and $X_7$ represents a nitro radical and the other represents a hydrogen or halogen atom or — in the case of $X_7$ — a cyano radical) by known methods for reducing a nitro radical to an amino radical, and then transforming the amino radical in the intermediate product obtained by known methods into a halogen atom or (when $X_7$ represented nitro) a cyano radical.

The reduction of the nitro radical to an amino radical is advantageously carried out in an acid medium, for example hydrochloric acid, in the presence of a metal, such as tin, at a temperature between 10° and 40° C.

When it is desired to obtain a compound of general formula I wherein $X_1$ or $X_2$ represents a chlorine atom, the product is generally obtained by decomposition, by cuprous chloride at a temperature between 20° and 70° C, of the diazonium salt prepared in situ in an aqueous medium at a temperature between −5° and +5° C by the action of sodium nitrite in the presence of an acid, such as hydrochloric acid, on the amine previously obtained.

When it is desired to obtain a compound of general formula I wherein $X_1$ or $X_2$ represents a fluorine atom, the product is generally obtained by decomposition at a temperature of about −10° C by means of hexafluorophosphoric acid, of the diazonium salt of the amine previously obtained.

When it is desired to obtain a compound of general formula I wherein $X_1$ represents a cyano radical, the product is generally obtained by decomposition, by means of potassium cyanide and copper sulphate, of the diazonium salt of the amine previously obtained. The reaction is advantageously carried out in an aqueous-organic medium, for example a mixture of water and toluene, at a temperature between 0° and 50° C.

When it is desired to obtain a compound of general formula I wherein $X_1$ or $X_2$ represents a bromine atom, the product is generally obtained by decomposition, by means of cuprous bromide in the presence of hydrobromic acid at a temperature between 20° and 70° C, of the diazonium salt prepared in an aqueous medium at a temperature between 5° and 15° C by the action of sodium nitrite in the presence of an acid, for example sulphuric acid,, on the amine previously obtained.

The compounds of general formula XIII wherein $X_6$ and $X_7$ are as hereinbefore defined can be obtained by nitration of a compound of general formula I in which at least one of the symbols $X_1$ and $X_2$ represents a hydrogen atom and $Y_1$ and $Y_2$ are as hereinbefore defined by application of the methods hereinbefore described for the preparation of the nitro compounds of general formula XII.

According to a still further feature of the present invention, the thiazolo[3,4-b]isoquinoline derivatives of general formula I wherein $X_1$ and $X_2$ are as hereinbefore defined, one of the symbols $Y_1$ and $Y_2$ represents a diacetylamino radical and the other represents a hydrogen or halogen atom or an alkyl, alkoxy or alkylthio radical, each of such radicals containing 1 to 4 carbon atoms, or a diacetylamino radical, are prepared by known methods for the conversion of an amino radical to a diacetylamino radical without affecting the rest of the molecule starting from a corresponding compound of general formula I wherein at least one of the symbols $Y_1$ and $Y_2$ represents the amino radical. Preferably acetic anhydride is reached with the amino starting material of general formula I and advantageously the reaction is effected at the boiling temperature of the reaction mixture.

The thiazolo[3,4-b]isoquinoline derivatives of general formula I obtained by the aforementioned processes can be purified by physical methods such as cyrstallisation or chromatography.

The thiazolo[3,4-b]isoquinoline derivatives of general formula I may be converted by known methods into acid addition salts. The acid addition salts may be obtained by the action of acids on the thiazolo[3,4-b]-isoquinoline derivatives in appropriate solvents. As organic solvents there may be used alcohols, ketones, ethers or chlorinated hydrocarbons. The salt which is formed is precipitated, if necessary after concentration of the solution, and is isolated by filtration or by decantation.

The thiazolo[3,4-b]isoquinoline derivatives of general formula I and their acid addition salts possess useful pharmacological properties. They are particularly active as anti-ulcer agents.

In rats they have shown an antagonistic activity vis-a-vis gastric acid secretion stimulated by histamine when administered orally at doses between 10 and 50 mg/kg animal body weight. Moreover they have been shown to be active at doses between 20 and 100 mg/kg animal body weight by oral administration against gastric ulcers induced experimentally in the rat according to the technique of Rossi et al., C.R. Soc. Biol., 150 2, 124 (1956).

Their toxicity in mice is greater than or equal to 100 mg/kg animal body weight by oral administration, and the greater proportion of them show no signs of toxicity in mice at doses of 900 mg/kg animal body weight by oral administration.

Of particular interest are those thiazolo[3,4-b]-isoquinoline derivatives of general formula I wherein $Y_1$ and $Y_2$ each represent a hydrogen atom or a methyl or diacetylamino radical, and more especially those compounds in which $X_1$ and $X_2$ and one of the symbols $Y_1$ and $Y_2$ represent hydrogen atoms. Of outstanding interest are (S)-3-(pyrid-2-yl-imino)-1,5,10,10a-tetrahydrothiazolo[3,4-b]isoquinoline, (S)-3-[(6-methylpyrid-2-yl)imino]-1,5,10,10a-tetrahydrothiazolo[3,4-b]isoquinoline and (S)-3-[(6-diacetylaminopyrid-2-yl)imino]-1,5,10,10a-tetrahydrothiazolo[3,4-b]isoquinoline, and acid addition salts thereof.

For therapeutic purposes, the thiazolo[3,4-b]isoquinoline derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates, and methylene-bis-β-hydroxynaphthoates) so that the beneficial physiological properties inherent in the bases are not vitiated by side effects ascribable to the anions.

The following Examples illustrate the invention.

EXAMPLE 1

A solution of (S)-3-hydroxymethyl-N-(pyrid-2-yl)-1,2,3,4-tetrahydroisoquinoline-2-carbothioamide (29.5 g) in 6N hydrochloric acid (350 cc) is heated at 100° C for 1 hour. After cooling, the solution is concentrated under reduced pressure (25 mm Hg) to one fifth of its volume, made alkaline by the addition of 10N sodium hydroxide solution (230 cc) and then extracted with methylene chloride (3 × 150 cc). The organic extracts are combined and dried over magnesium sulphate. After filtration and concentration to dryness of the filtrate under reduced pressure (25 mm Hg), a cream coloured solid (22 g) is obtained. This solid is dissolved in boiling isopropanol (200 cc), decolourizing charcoal (2 g) is added and the mixture is filtered. After cooling the resulting while crystals are filtered off and washed with cold isopropanol (3 × 10 cc). After drying at 60° C under reduced pressure (1 mm Hg) (S)-3-(pyrid-2-ylimino)-1,5,10,10a-tetrahydrothiazolo[3,4-b]isoquinoline (11.9 g), melting at 125° C is obtained.

$[\alpha]_D^{20} = -245° \pm 3°$ (c = 2, chloroform).

(S)-3-Hydroxymethyl-N-(pyrid-2-yl)-1,2,3,4-tetrahydroisoquinoline-2-carbothioamide can be prepared as follows:

2-Isothiocyanatopyridine (13.6 g) is added to a solution of (S)-3-hydroxymethyl-1,2,3,4-tetrahydroisoquinoline (16.3 g) in ethanol (300 cc) and the mixture is heated under reflux for 1 hour. The suspension gradually becomes a solution whilst the colour of the solution changes from orange to yellow. The solution is then left for 15 hours at a temperature of about 20° C after which it is concentrated to dryness under reduced pressure (25 mm Hg). (S)-3-Hydroxymethyl-N-(pyrid-2-yl)-1,2,3,4-tetrahydroiosoquinoline-2-carbothioamide (29.5 g) is obtained in the form of a light yellow solid.

(S)-3-Hydroxymethyl-1,2,3,4-tetrahydroisoquinoline can be prepared according to the method of S. Yamada and T. Kunieda, Chem. Pharm. Bull., 15 490 (1967).

2-Isothiocyanatopyridine, which exists in the form of a dimer, can be prepared according to the method of A. Fairfull and D. Peak, J. Chem. Soc., 798, 1955.

EXAMPLE 2

A suspension of 2-aminopyridine (1.0 g) in acetonitrile (15 cc) is added slowly, whilst stirring, to a suspension of (S)-3-chloro-1,5,10,10a-tetrahydrothiazolo[3,4-b]isoquinolinium chloride (2.6 g) in acetonitrile (25 cc), after which triethylamine (2.9 cc) in acetonitrile (5 cc) is added dropwise. A slight rise in temperature of the reaction mixture and partial dissolution of the suspension followed by the formation of a precipitate, are observed. The reaction mixture is stirred for 2 hours at a temperature of about 20° C and is then evaporated under reduced pressure (25 mm Hg). The residue is dissolved in a mixture of water (50 cc) and methylene chloride (100 cc). The organic phase after decantation is extracted with 1N hydrochloric acid (2 × 50 cc). The aqueous extracts are combined, made alkaline by addition of a 10N sodium hydroxide solution and extracted with methylene chloride (2 × 50 cc). The organic phase is washed with water and dried over magnesium sulphate. After filtration and concentration to dryness under reduced pressure (25 mm Hg), (S)-3-(pyrid-2-ylimino)-1,5,10,10a-tetrahydrothiazolo[3,4-b]isoquinoline (1.0 g), melting at 120° C is obtained. After recrystallisation from a mixture of toluene and diisopropyl ether (1:3 by volume), a product the characteristics of which are identical to those of the product of Example 1 is obtained.

(S)-3-Chloro-1,5,10,10a-tetrahydrothiazolo[3,4-b]isoquinolinium chloride can be prepared in the following manner:

A solution (20 cc) of phosgene in toluene (containing 2 mols of phosgene per liter) is added dropwise in the absence of moisture whilst stirring and at a temperature of about 20° C to a solution of (S)-1,5,10,10a-tetrahydrothiazolo[3,4-b]isoquinoline-3-thione (2.2 g) in tetrahydrofuran (25 cc). The mixture becomes cloudy after 15 minutes; it is stirred for 5 hours and heated at 50° C for 1 hour. The solvents are evaporated under reduced pressure (25 mm Hg) to give (S)-3-chloro-1,5,10,10a-tetrahydrothiazolo[3,4-b]isoquinolinium chloride (2.6 g) in the form of a very hygroscopic white crystalline powder.

(S)-1,5,10,10a-Tetrahydrothiazolo[3,4-b]-isoquinoline-3-thione can be prepared in the following manner:

Carbon disulphide (40 g) is added dropwise, with vigorous stirring, to a solution of (S)-3-hydroxysulphonyloxymethyl-1,2,3,4-tetrahydroisoquinoline (100 g) in 0.25N sodium hydroxide solution (4000 cc). The reaction is exothermic. A solid precipitates. Stirring is continued for a further 3 hours and then the reaction mixture is neutralised by the addition of 4N hydrochloric acid. The resulting crystals are filtered off, washed copiously with water and then recrystallised from ethanol (3000 cc). (S)-1,5,10,10a-Tetrahydrothiazolo[3,4-b]isoquinoline-3-thione (77 g) is thus obtained in the form of fine white needles melting at 150° C.

$[\alpha]_D^{20} = -377° \pm 4°$ (c = 1; chloroform).

(S)-3-Hydroxysulphonyloxymethyl-1,2,3,4-tetrahydroisoquinoline can be prepared in the following manner:

A solution of (S)-3-hydroxymethyl-1,2,3,4-tetrahydroisoquinoline (41 g) in a mixture of sulphuric acid (d = 1.83; 13 cc) and water (70 cc) is heated at 110° C. Water (50 cc) is distilled off and the mixture is then concentrated under reduced pressure (20 mm Hg) at 100° C. The brown oily residue is taken up in a mixture of sulphuric acid (d = 1.83; 13 cc) and water (70 cc). Water (50 cc) is again distilled off and the mixture is then concentrated as previously described, after which the concentration is finished at 100° C under reduced pressure (1 mm Hg). The residue which crystallises on cooling, is redissolved in a hot mixture of ethanol (140 cc) and water (60 cc). After cooling for 15 hours at about 5° C the resulting crystals are filtered off and washed with a mixture (20 cc) of ethanol and water (3:1 by volume) and then with ethanol (2 × 25 cc). After drying at 60° C under reduced pressure (1 mm Hg), (S)-3-hydroxysulphonyloxymethyl-1,2,3,4-tetrahydroisoquinoline (48 g) is obtained in the form of white crystals.

$[\alpha]_D^{20} = -55° \pm 1°$ (c = 1; dimethylsulphoxide).

EXAMPLE 3

(S)-3-Methylthio-1,5,10,10a-tetrahydrothiazolo[3,4-b]isoquinolinium iodide (18.2 g) is added to a solution of 2-amino-6-methylpyridine (10.8 g) in pyridine (300 cc). After 18 hours at a temperature of about 20° C, dissolution is complete and the reaction mixture is left to stand for 2 hours. The solution is concentrated to dryness under reduced pressure (25 mm Hg) and the residue is dissolved in a mixture of water (300 cc) and methylene chloride (300 cc). The organic phase is decanted, dried over magnesium sulphate, filtered and then concentrated to dryness under reduced pressure (20 mm Hg). Propanol (350 cc) is added to the residue obtained, the mixture is heated to the boiling point and filtered whilst hot. After cooling to 5° C, the resulting crystals are filtered off and washed with propanol (3 × 20 cc). After drying at 60° C under reduced pressure (1 mm Hg) (S)-3-[(6-methylpyrid-2-yl)imino]-1,5,10,10a-tetrahydrothiazolo[3,4-b]isoquinoline (12.0 g) is obtained in the form of white crystals melting at 167° C.

$[\alpha]_D^{20} = -254° \pm 2°$ (c = 2, chloroform).

EXAMPLE 4

(S)-3-Methylthio-1,5,10,10a-tetrahydrothiazolo[3,4-b]isoquinolinium iodide (20 g) is added in small portions to a solution of 2,6-diaminopyridine (60 g) in pyridine (400 cc). The suspension passes rapidly into solution. After 15 hours at a temperature of about 20° C the solution is concentrated to dryness under reduced pressure (25 mm Hg). The residue is taken up in methylene chloride (500 cc); the insoluble material (47 g) consists of 2,6-diaminopyridine. The methylene chloride solution is washed with water (3 × 100 cc), dried over magnesium sulphate, filtered and then concentrated to dryness under reduced pressure (20 mm Hg). After addition to the residue obtained of a mixture (250 cc) of water and ethanol (4:1 by volume) the mixture is heated to the boiling point. After cooling to 5° C the resulting crystals are filtered off and washed with ethanol (50 cc) to give (S)-3-[(6-aminopyrid-2-yl)imino]-1,5,10,10a-tetrahydrothiazolo[3,4-b]isoquinoline (11 g) in the form of white crystals melting at 128° C.

$[\alpha]_D^{20} = -270° \pm 3°$ (c = 1; chloroform).

EXAMPLE 5

A solution of (S)-3-[(6-aminopyrid-2-yl)imino]-1,5,10,10a-tetrahydrothiazolo[3,4-b]isoquinoline (1.0 g) in acetic anhydride (15 cc) is heated under reflux for 30 minutes. The reaction mixture is then dried under reduced pressure (25 mm Hg). The residue is dissolved in a mixture of methylene chloride (20 cc) and water (15 cc). The organic phase is decanted, dried over magnesium sulphate, filtered and then concentrated to dryness. The oily residue is dissolved in boiling ethanol (15 cc). After cooling, the resulting crystals are filtered off, washed with ethanol (5 cc) and dried to give (S)-3-[(6-diacetylaminopyrid-2-yl)imino]-1,5,10,10a-tetrahydrothiazolo[3,4-b]isoquinoline (0.8 g) in the form of white crystals melting at 167° C.

$[\alpha]_D^{20} = -188° \pm 2°$ (c = 1; chloroform).

The present invention includes within its scope pharmaceutical compositions comprising, as active ingredient, at least one of the compounds of general formula I, or a non-toxic acid addition salt thereof, in association with a pharmaceutical carrier or coating. The invention includes especially such preparations made up for oral, parenteral, rectal or topical, particularly dermal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in a sterile injectable medium immediately before use.

Compositions for rectal admistration are suppositories which contain, in addition to the active substance, excipients such as cacao butter or a suitable wax base.

Compositions for topical administration include ointments.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy for the treatment of medicinal and other gastritis and gastralgias and the treatment of ulcers (gastric and duodenal ulcers and peptic ulcers). In human therapy the compositions when administered to an adult should generally give doses between 1 mg and 200 mg of active substance per day. In general the physician will decide the posology considered appropriate, taking into account the age and weight and other factors intrinsic to the patient being treated.

The following Example illustrates pharmaceutical compositions according to the invention.

EXAMPLE 6

Tablets containing the active product and having the following composition are prepared in accordance with the usual technique:

| | |
|---|---|
| (S)-3-[(6-methylpyrid-2-yl)imino]-1,5,10,10a-tetrahydrothiazolo[3,4-b]isoquinoline | 200 mg |
| starch | 60 mg |
| precipitated silica | 38 mg |
| magnesium stearate | 2 mg |

We claim:
1. A thiazolo[3,4-b]isoquinoline derivative of the formula:

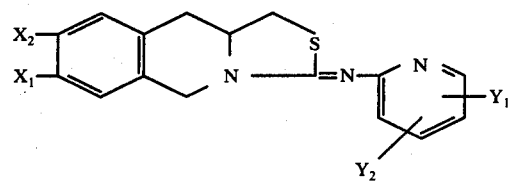

wherein $X_1$ represents hydrogen, halogen, methoxy or cyano, $X_2$ represents hydrogen, halogen or methoxy, or $X_1$ and $X_2$ together represent methylenedioxy, and $Y_1$ and $Y_2$ each represent hydrogen, halogen, alkyl of 1 through 4 carbon atoms, alkoxy of 1 through 4 carbon atoms, alkylthio of 1 through 4 carbon atoms, hydroxy, or diacetylamino, and its non-toxic pharmaceutically acceptable acid addition salts.

2. A thiazolo[3,4-b]isoquinoline derivative according to claim 1 wherein $Y_1$ and $Y_2$ each represent hydrogen, methyl or diacetylamino, and its non-toxic pharmaceutically acceptable acid addition salts.

3. A thiazolo[3,4-b]isoquinoline derivative according to claim 1 wherein $X_1$ and $X_2$ and one of the symbols $Y_1$ and $Y_2$ represent hydrogen atoms, and its non-toxic pharmaceutically acceptable acid addition salts.

4. A thiazolo[3,4-b]isoquinoline derivative according to claim 1 wherein $X_1$, $X_2$ and $Y_1$ represent hydrogen, and $Y_2$ represents hydrogen, methyl, or diacetylamino, and its non-toxic pharmaceutically acceptable acid addition salts.

5. A compound according to claim 1 which is (S)-3-(pyrid-2-ylimino)-1,5,10,10a-tetrahydrothiazolo[3,4-b]isoquinoline, and its non-toxic pharmaceutically acceptable acid addition salts.

6. A compound according to claim 1 which is (S)-3-[(6-methylpyrid-2-yl)imino]-1,5,10,10a-tetrahydrothiazolo[3,4-b]isoquinoline and its non-toxic pharmaceutically acceptable acid addition salts.

7. A compound according to claim 1 which is (S)-3-[(6-diacetylaminopyrid-2-yl)imino]-1,5,10,10a-tetrahydrothiazolo[3,4-b]isoquinoline and its non-toxic pharmaceutically acceptable acid addition salts.

8. A pharmaceutical composition for the treatment of medicinal and other gastritis and gastralgias and the treatment of ulcers which comprises an effective amount of a thiazolo[3,4-b]isoquinoline derivative as claimed in claim 1, or a non-toxic pharmaceutically acceptable acid addition salt thereof, in association with a pharmaceutically acceptable carrier.

9. A method for the treatment of medicinal and other gastritis and gastralgias and the treatment of ulcers in a patient which comprises administering to the patient an effective amount of a thiazolo[3,4-b]isoquinoline derivative as claimed in claim 1 or a non-toxic pharmaceutically acceptable acid addition salt thereof.

* * * * *

UNITED STATES PATENT AND TRADEMARK OFFICE
CERTIFICATE OF CORRECTION

PATENT NO. : 4,108,999
DATED : August 22, 1978
INVENTOR(S) : Daniel FARGE et al

It is certified that error appears in the above-identified patent and that said Letters Patent are hereby corrected as shown below:

Under the section entitled "[75] Inventors:", the residences of two of the inventors should be corrected as follows:

after "Daniel Farge", delete "Sylvestres";

after "Daniel Reisdorf", delete "Republique-".

In both cases these terms are part of the street addresses, and the place of residence is simply "Thiais".

Signed and Sealed this

Seventeenth Day of April 1979

[SEAL]

Attest:

RUTH C. MASON
Attesting Officer

DONALD W. BANNER
Commissioner of Patents and Trademarks